May 9, 1972 T. YUGE Plant Pat. 3,155
AZALEA PLANT
Filed July 13, 1970
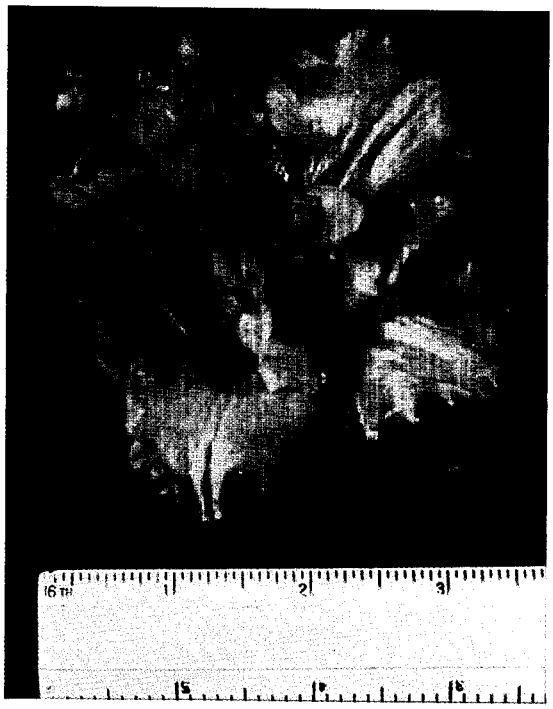
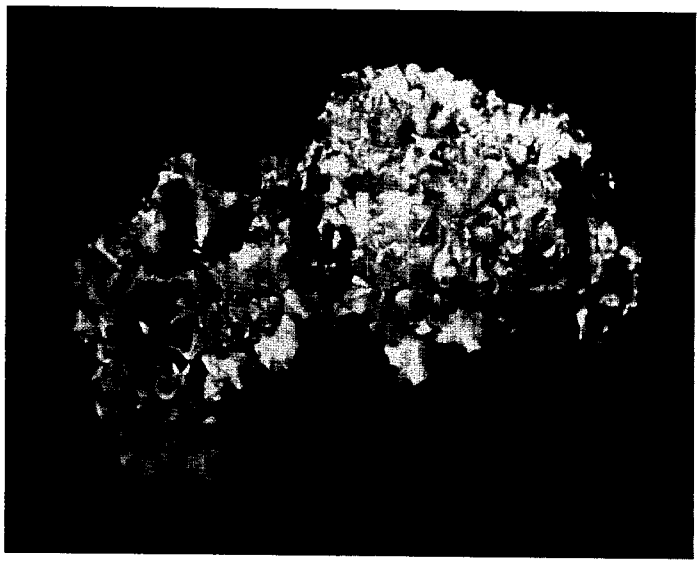
INVENTOR.
TAKEO YUGE
BY Rummler & Snow
Attys

United States Patent Office

Plant Pat. 3,155
Patented May 9, 1972

3,155

AZALEA PLANT

Takeo Yuge, Altadena, Calif., assignor to Geo. J. Ball, Inc., West Chicago, Ill.

Filed July 13, 1970, Ser. No. 54,667
Int. Cl. A01h *5/00*
U.S. Cl. Plt.—57 1 Claim

ABSTRACT OF THE DISCLOSURE

An improved variety of red flowered azalea plant particularly adapted for greenhouse pot-forcing characterized by its profuse production of very large, highly frilled, long lasting, bright red blossoms which are presented very upright in candle style.

BACKGROUND OF THE INVENTION

My new variety of azalea plant was developed by me in the course of a breeding program carried on at Altadena, Calif., with the object of producing improved types of greenhouse pot-forcing plants capable of profuse production of extraordinary and attractive blossoms. The present variety is a result of crossing Miss Cottage Gardens (unpatented) with Kaho (unpatented) as the pollen parent and this seedling was selected because it appeared to possess the most desirable characteristics of flower production, growth habit, form and color of bloom, and lasting quality as a flowered plant. Asexual reproduction of this new plant at Altadena, Calif., by cuttings, through several generations, has demonstrated its novel and distinctive characteristics to be fixed and to hold true from generation to generation. Propagation of the new variety, for commercial purposes, is now being done, by cuttings, at Salem, Oreg., and at San Fernando, Calif.

DESCRIPTION OF THE DRAWING

My new variety of azalea plant is illustrated by the accompanying photographically reproduced drawing in which the upper view shows a single blossom in close-up detail, and the lower view shows a typical specimen of the potted plant in full bloom.

DESCRIPTION OF THE NEW AZALEA VARIETY

The following is a detailed description of my new variety of azalea plant with designations of color according to the Horticultural Colour Chart of the British Colour Council.

*The plant*

Origin: Seedling.
Parentage:
*Seed parent.*—Miss Cottage Gardens (unpatented).
*Pollen parent.*—Kaho (unpatented).
Classification: Botanic—Belgian Indica.
Form: Bush—height—medium.
Growth: Vigorous, sturdy and much branched.
Foliage: Quantity—abundant.
Leaf Shape.—Elliptic, with hirsute edges. Size: 2½ inches long when mature. Texture—leathery.
*Color.*—Upper side—Near Ivy Green 0001060/3. Under side—Spinach Green 0960/2.
*Petioles.*—¼ inch long.
*Ribs and veins.*—Alternate.
*Rachis.*—Flat-topped hirsute.

*The bud*

Size: Moderately large.
Form: Pointed and long, with irregular shape—diameter—¾ inch—depth—1¾ inches.
Opening: Bud opens slowly.
Color:
*When sepals first divide.*—Indian Lake 826.
*When petals begin to unfurl.*—Cardinal Red 822/3.
Sepals: Stand up. Color—inside—Scheeles Green 860/2—outside—Scheeles Green 860/3.
Calyx: Funnel shaped. Splits and has a hairy aspect.
Peduncle: ¼ inch long, erect and hairy. Color—Pod Green 061. Usually with a reddish overcast.

*The flower*

Blooming habit: Recurrent. Plant blooms profusely, once each spring, from midseason to late.
Size: Very large. Up to 3½ inches in diameter and to 2 inches in depth.
Borne: In clusters.
Shape: Funnel-form when flower first opens and this shape persists.
Petalage: Number of petals—5, 6 or 7.
*Form.*—Frilled.
*Arrangement.*—Fused, lobed and semi-double.
*Color.*—Standard and Upper Wings—Rose Red 724 blotched and shaded with Cardinal Red 822. Rose Opal 022 at base. Lower Wings—inside—Rose Red 724—reverse side—Rose Red 724.
*Appearance.*—Satiny.
*Discoloration.*—Color changes to Rose Madder 23 after full bloom.
Petaloids: Usually 8 in number. Of medium size and Rose Red 724 in color.
Peduncle: Upright, ¼ inch in length. Color—Pod Green 061, sometimes overcast with red.
Fragrance: Slight.
Persistence: Flower does not hang on and dry.
Lasting quality: Long lasting on plant, with excellent keeping quality.

*Reproductive organs*

Stamens: Anthers—usually 8 in number, 1¼ inches long and of very irregular shape fused to petaloids.
Pollen: Color—Pale Yellow (general color term).
Pistils: One, ¾ to 1 inch in length.
Stigmas: Brownish in color.

My new variety of azalea plant is distinguished by its bright red, highly frilled flower which is presented generally in a very upright style and which has a very excellent keeping quality. The abundant foliage and profuse blooming habit, particularly adapted to greenhouse pot-forcing, also contribute to the desirability of this new variety for production for retail sale by the florist trade.

I claim:

1. A new and distinct variety of azalea plant substantially as herein shown and described, characterized by its very large, bright red, highly frilled flowers which are produced profusely and presented in a very upright style, by its vigorous growth habit, by its adaptability for greenhouse pot-forcing, and by the excellent keeping quality of the blooms on the plant.

No references cited.

ROBERT E. BAGWILL, Primary Examiner